(12) United States Patent
Bryson et al.

(10) Patent No.: US 7,556,819 B1
(45) Date of Patent: Jul. 7, 2009

(54) SKIN COMPOSITION

(75) Inventors: Paul Harold Bryson, Hidden Hills, CA (US); Vartan Libaridian, Van Nuys, CA (US); Michelle Volynsky, Tarzana, CA (US)

(73) Assignee: OPI Products, Inc., North Hollywood, CA (US)

( * ) Notice: Subject to any disclaimer, the term of this patent is extended or adjusted under 35 U.S.C. 154(b) by 567 days.

(21) Appl. No.: 10/628,033

(22) Filed: Jul. 25, 2003

(51) Int. Cl.
*A61K 8/02* (2006.01)

(52) U.S. Cl. ..................... 424/401; 424/70.1

(58) Field of Classification Search .............. 424/401, 424/725, 70.1
See application file for complete search history.

(56) References Cited

U.S. PATENT DOCUMENTS

| | | | | |
|---|---|---|---|---|
| 4,818,523 A | * | 4/1989 | Clarke et al. | 424/70.12 |
| 6,709,663 B2 | * | 3/2004 | Espinoza | 424/401 |
| 6,927,205 B2 | * | 8/2005 | Patt | 514/6 |

OTHER PUBLICATIONS

Flick, E., "Ultra Skin Treatment Cream", Cosmetic and Toiletry Formulations, 1997, (2nd ed.), vol. 6, p. 148.*
Flick, E., Cosmetic and Toiletry Formulations, 2001, Noyes Publications, 2nd Ed., vol. 8, p. 30.*
Braun, D., et al., Rheology Modifiers Handbook, 1999, William Andrew Publishing, p. 377.*
Flick, E., Cosmetic and Toiletry Formulations, 1997, Noyes Publications, 2nd Ed. vol. 6, pp. 150 and 209.*
Flick, E., Cosmetics and Additives; An Industrial Guide, 1991, Noyes Publications, p. 415.*
Flick, E., Cosmetic and Toiletry Formulations, 1997, Noyes Publications, $2^{nd}$ ed., vol. 6, p. 37.*
"Ultrasil Q-Plus Quaternary Silicone," Noveon Technical Data Sheet, TDS-322, Jan. 15, 2003, pp. 1-3.

* cited by examiner

*Primary Examiner*—Gina C. Yu
(74) *Attorney, Agent, or Firm*—Blakely, Sokoloff, Taylor & Zafman

(57) ABSTRACT

In one embodiment, there is disclosed a composition including water, a glycol, a silicone, a quaternium, and a polymer viscosity modulator.

15 Claims, 1 Drawing Sheet

SKIN COMPOSITION

BACKGROUND

1. Field

A composition for application to the skin.

2. Related Art

Compositions for application to the skin or hair are generally known in the art.

U.S. Pat. No. 6,153,204 discloses cosmetic or pharmaceutical preparations characterized in that they comprise an effective concentration of hydrophilic starch esterified with one or more n-octenylsuccinate radicals.

U.S. Pat. No. 6,372,203 discloses a hair treatment composition that contains one or more polymers or copolymers, each of which is made from one or more monomers, in a cosmetic foundation. The respective monomers are selected from the group consisting of ethylenic unsaturated saccharides, ethylenic unsaturated saccharic acids, derivatives of ethylenic unsaturated saccharides and derivatives of ethylenic unsaturated saccharic acids. The unsaturated saccharides and saccharic acids are present in cyclic or open chain form.

U.S. Pat. No. 6,432,393 discloses aqueous hair care compositions including conditioners, shampoos, and mousses. There is also disclosed methods of treating hair, and more particularly to treating hair with aqueous hair care compositions which contain one or more elastomeric resinous materials. These materials when tested at the same concentration that could be incorporated into a product exhibit a G' modulus between $1\times10^2$ and $1\times10^5$ dynes/cm$^2$. Furthermore these resins when mixed with a hydrophilic or hydrophobic diluent at a ratio of 1:95 to 95:1% and this mixture then incorporated into an aqueous emulsion in the range of 0.1 to 10% have been demonstrated to deliver a consumer perceptible increase in hair body without sacrificing conditioning attributes.

U.S. Pat. No. 6,451,298 discloses cosmetic compositions including at least one silicone copolymer with a dynamic viscosity ranging from $1\times10^6$ to $100\times10^6$ cP and at least one cationic polymer. This combination can give cosmetic properties, such as at least one of smoothness, lightness, and softness, without the phenomenon of regreasing keratin fibers. These compositions can be used for washing and/or conditioning a keratin material, such as the hair or the skin.

U.S. Pat. No. 6,475,475 discloses combinations of polymer compounds and hair treatment compositions, with film-forming properties and improved hair-fixing properties, particularly increased elasticity of the polymer film or the treated hair. The polymer compound combinations include at least one terpolymer of vinyl pyrrolidone, vinyl caprolactam and basic acryl amide monomer and at least one anionic or anionizable polymer with anionic or anionizable groups.

U.S. Pat. No. 6,511,655 discloses low-viscosity cosmetic or dermatological preparations of the oil-water type, which include an oil phase, in which phydrophobic and/or amphiphilic solids are incorporated, and a water phase, where the difference in density between the oil phase and the water phase (determinable using a computerized digital density meter of the type DMA 45 from chempro/PA at 25° C.) is not greater than 0.01 gcmr$^3$, and disclosed is a method of stabilizing oil-water formulations.

U.S. Pat. No. 6,524,594 discloses a gelled oil composition containing an emulsifier, a gelling agent, an oil, and a surfactant which, when applied to the skin in the presence of water, produces a significant amount of foam. After the composition is rinsed from the skin, a non-greasy, oil residue is left thereon.

U.S. Pat. No. 6,524,598 discloses cosmetic compositions including a combination of non-emulsifying and emulsifying crosslinked siloxane elastomers.

DETAILED DESCRIPTION

Figure 1:
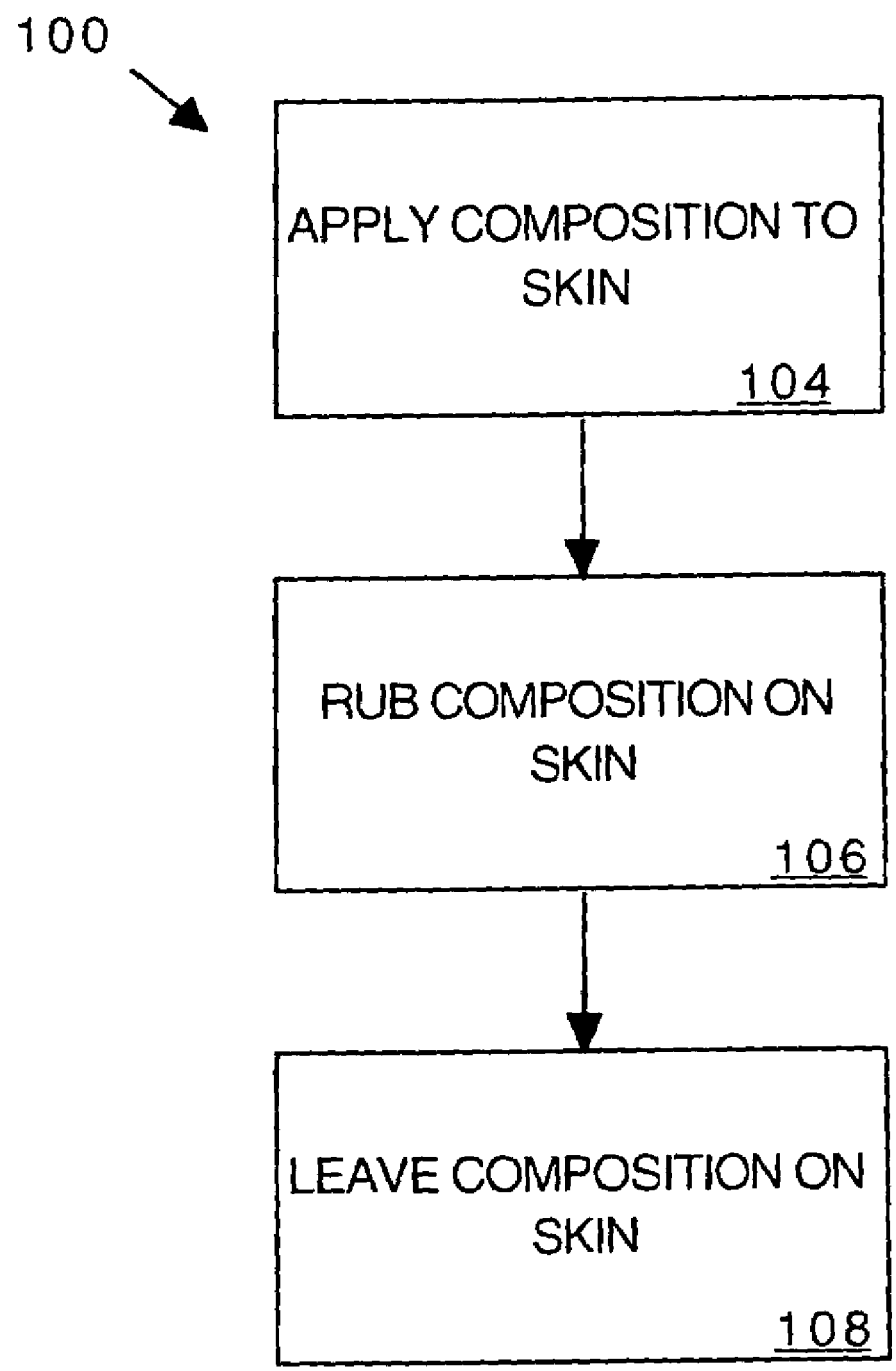
FIG. 1 is a flow diagram showing a method of treating the skin.

In one embodiment, there is disclosed a composition including water, a glycol, a silicone, a quaternium, and a polymer viscosity modulator. In one embodiment, the composition has a pH of less than about 3.5. In another embodiment, the composition has a pH in a range of about 2.8 to about 3.2. In another embodiment, the composition has a pH of about 3.

In one embodiment, the composition does not include an alpha-hydroxy acid such as glycolic acid or lactic acid. In another embodiment, the composition includes less than about five percent, by weight of an alpha-hydroxy acids. In another embodiment, the composition includes less than about three percent by weight of an alpha-hydroxy acids. In another embodiment, the composition includes less than about one percent by weight of an alpha-hydroxy acid. In another embodiment, the composition includes less than about 0.1 percent by weight of an alpha-hydroxy acid.

Suitable compositions include the following by weight:

- 1-10% glycol;
- 2-30% silicone;
- 0.1-20% quaternium;
- 0.1-1% polymer viscosity modifier; and
- 60-90% water.

Suitable glycols include, but are not limited to, dihydric alcohols, propylene glycol, butylene glycol, ethylene glycol, ethoxy diglycol, and mixtures and blends thereof. Suitable glycols also include, but are not limited to, alkoxydiglycols (for example methoxydiglycol, ethoxydiglycol, propoxydiglycol, butoxydiglycol), and $C_1$ to $C_4$ glycols. In one embodiment, a suitable glycol is propylene glycol commercially available from Coast Chemicals of Los Angeles, Calif., under the name Propylene Glycol USP Kosher.

In another embodiment, a polyhydric alcohol may be used instead of a glycol or in combination with a glycol. Suitable polyhydric alcohols include, but are not limited to, trihydric alcohols, glycyl alcohol, glycerin, and mixtures and blends thereof.

Suitable silicones include, but are not limited to, siloxane polymers, cyclomethicones, dimethicones, amodimethicones, trimethicones, copolymers of dimethicone and another component (such as polyols), emulsifiable silicones, and copolymers of trimethicone and another component (such as polyols). In one embodiment, suitable silicones include dimethicone.

Dimethicone is commercially available from Shinetsu Chemicals Ltd. of Tokyo, Japan, under the product name DM Fluid A6T.

Suitable quaterniums include, but are not limited to, quaternary ammonium salts, quaternary ammonium compounds, a molecular structure including a central nitrogen atom joined to four organic groups, behentrimonium methosulfate, cetearyl alcohol, and mixtures and blends thereof. In another embodiment, suitable quaterniums include monomethyl-substituted quaternary nitrogen, dimethyl-substituted quaternary nitrogen, trimethyl-substituted quaternary nitrogen, quaternary ammonium salts, for example polyquaternium-20, polyquaternium-82, polyquaternium-37, and quaternium-15.

In one embodiment, a suitable quaternium is INCROQUAT BEHENYL TMS™ available from Croda, Inc. of Parsippany, N.J.

Suitable polymer viscosity modulators include, but are not limited to a blend of polyquaternium-37, propylene glycol dicaprylate/dicaprate, and PPG-1 Trideceth-6, available from Cosmetic Rheologies Ltd. of Manchester, United Kingdom, under the product name Rheocare CTH(E).

In another embodiment, the composition includes vegetable oil. In another embodiment, a suitable vegetable oil includes avocado oil.

In another embodiment, the composition also includes at least one material selected from ascorbyl palmitate, tocopherol, aloe barbadensis, aloe vera extract, persea gratissima, avocado oil, ethylhexyl palmitate, lecithin, capric triglyceride, caprylic triglyceride, isopropylparaben, isobutylparaben, butylparaben, methylparaben, alcohol, BHT, and blends and mixtures thereof. In other embodiments, two or more of the listed materials are included in the composition.

In another embodiment, the composition is in the form of an oil in water emulsion.

For a composition having a pH less than about 3.5, such composition may have exfoliant properties. In one embodiment, the composition is suitable for application to human skin (e.g., face and body). Referring to FIG. 1, there is illustrated method 100 of exfoliating skin by: applying a quantity of a composition. A composition is applied to a portion or area of the skin 104, and is rubbed on the skin 106. Once distributed, the composition is retained or left on the skin 108.

In another embodiment, the composition includes a fragrance, perfume, and/or a coloring agent.

The wide range of permissible weight percent contributions of the different components of the composition reflects, in one aspect, tradeoffs that exist with the manufacture of the composition. Typically, the lowest cost component in the composition is the water. Because the other ingredients may provide for a conditioning action and/or an exfoliating action of the composition, a tradeoff exists between cost, conditioning action, exfoliating action, and/or the antiseptic and fragrance properties of the composition.

In the foregoing specification, compositions and methods have been described with reference to specific embodiments thereof. It will, however, be evident that various modifications and changes can be made thereto without departing from the broader spirit and scope of the appended claims. The specification and drawings are, accordingly, to be regarded in an illustrative rather than a restrictive sense.

EXAMPLE 1

A composition was prepared by emulsifying the components at 70° C., where the composition has the following formula:

| | |
|---|---|
| Deionized water | 86.4% |
| Propylene glycol | 5% |
| Dimethicone | 4% |
| Blend of behentrimonium methosulfate and cetearyl alcohol | 3% |
| Blend of isopropylparaben, isobutylparaben, and butylparaben | 0.5% |
| Benzophenone-3 | 0.5% |
| Blend of polyquaternium-37 propylene glycol dicaprylate/dicaprate, and PPG-1 trideceth-6 | 0.2% |
| Berry Fragrance | 0.15% |
| Allantoin | 0.1% |

-continued

| | |
|---|---|
| BHT | 0.05% |
| Benzophenone-4 | 0.05% |
| Ascorbyl palmitate | 0.01% |
| Tocopherol | 0.01% |
| Aloe barbadensis (aloe vera) leaf extract | 0.01% |
| Avoplex ® blend of persea gratissima (avocado) oil, ethylhexyl palmitate, lecithin, caprylic/capric triglyceride, methylparaben, and alcohol | 0.01% |
| CI 17200 (red 33) | 0.00061% |
| CI 42090 (blue 1) | 0.00052% |
| Vaccinium angustifolium (blueberry) fruit extract | 0.00029% |
| Rubus idaeus (raspberry) fruit extract | 0.00029% |
| Fragaria vesca (strawberry) fruit extract | 0.00029% |

(Percentages measured by weight)

EXAMPLE 2

A composition was prepared by emulsifying the components at 70° C., where the composition has the following formula:

| | |
|---|---|
| Deionized water | 86.7% |
| Propylene glycol | 5% |
| Dimethicone | 4% |
| Blend of behentrimonium methosulfate and cetearyl alcohol | 3% |
| Blend of isopropylparaben, isobutylparaben, and butylparaben | 0.5% |
| Peach fragrance | 0.4% |
| Blend of polyquaternium-37 propylene glycol dicaprylate/dicaprate, and PPG-1 trideceth-6 | 0.2% |
| Allantoin | 0.1% |
| BHT | 0.05% |
| Benzophenone-4 | 0.05% |
| Ascorbyl palmitate | 0.01% |
| Tocopherol | 0.01% |
| Aloe barbadensis (aloe vera) leaf extract | 0.01% |
| Avoplex ® blend of persea gratissima (avocado) oil, ethylhexyl palmitate, lecithin, caprylic/capric triglyceride, methylparaben, and alcohol | 0.01% |
| Prunus persica (peach) fruit extract | 0.001% |
| CI 47005 (yellow 10) | 0.00230% |
| CI 26100 (red 17) | 0.00011% |

(Percentages measured by weight)

EXAMPLE 3

A composition was prepared by emulsifying the components at 70° C., where the composition has the following formula:

| | |
|---|---|
| Deionized water | 86.5% |
| Propylene glycol | 5% |
| Dimethicone | 4% |
| Blend of behentrimonium methosulfate and cetearyl alcohol | 3% |
| Blend of isopropylparaben, isobutylparaben, and butylparaben | 0.5% |
| Pear fragrance | 0.5% |
| Blend of polyquaternium-37 propylene glycol dicaprylate/dicaprate, and PPG-1 trideceth-6 | 0.2% |
| Allantoin | 0.1% |
| BHT | 0.05% |
| Benzophenone-4 | 0.05% |
| Ascorbyl palmitate | 0.01% |
| Tocopherol | 0.01% |
| Aloe barbadensis (aloe vera) leaf extract | 0.01% |
| Avoplex ® blend of persea gratissima (avocado) oil, ethyihexyl palmitate, lecithin, caprylic/capric triglyceride, methylparaben, and alcohol | 0.01% |

-continued

| | |
|---|---|
| Pyrus communis (pear) fruit extract | 0.001% |
| CI 47005 (yellow 10) | 0.00055% |
| CI 42090 (blue 1) | 0.00026% |

(Percentages measured by weight)

EXAMPLE 4

Grapefruit Flavor

A composition was prepared by emulsifying the components at 70° C., where the composition has the following formula:

| | |
|---|---|
| Deionized water | 86.5% |
| Propylene glycol | 5% |
| Dimethicone | 4% |
| Blend of behentrimonium methosulfate and cetearyl alcohol | 3% |
| Blend of isopropylparaben, isobutylparaben, butylparaben | 0.5% |
| Grapefruit fragrance | 0.5% |
| Blend of polyquaternium-37 propylene glycol dicaprylate/dicaprate, and PPG-1 trideceth-6 | 0.2% |
| Allantoin | 0.1% |
| BHT | 0.05% |
| Benzophenone-4 | 0.05% |
| Benzophenone-2 | 0.05% |
| Ascorbyl palmitate | 0.01% |
| Tocopherol | 0.01% |
| Aloe barbadensis (aloe vera) leaf extract | 0.01% |
| Avoplex ® blend of persea gratissima (avocado) oil, ethylhexyl palmitate, lecithin, caprylic/capric triglyceride, methylparaben, and alcohol | 0.01% |
| Citrus grandis (grapefruit) fruit extract | 0.001% |
| CI 26100 (red 17) | 0.00044% |
| CI 17200 (red 33) | 0.00034% |

(Percentages measured by weight)

What is claimed is:

1. A composition consisting essentially of:
a glycol;
a silicone, wherein the amount of silicone present in the composition is 4% to 30% by weight;
a quaternium, wherein the amount of quaternium present in the composition is 3% to 20% by weight;
a polymer viscosity modulator, wherein the amount of polymer viscosity modulator present in the composition is 0.2% to 1% by weight and the polymer viscosity modulator is a blend of polyquaternium-37 propylene glycol dicaprylate/dicaprate and PPG-1 trideceth-6; and
wherein the composition is in the form of a body lotion that is suitable for being left on the skin such that it exfoliates the skin in the absence of an alpha-hydroxy acid and has a pH in a range of 2.8 to 3.2.

2. The composition of claim 1, wherein the composition has a pH of 3.

3. The composition of claim 1, comprising:
about 1% to about 10% glycol by weight; and
about 60% to about 90% water by weight.

4. The composition of claim 1, wherein the glycol comprises a material selected from the group consisting of propylene glycol, butylene glycol, glycerin, ethoxy diglycol, and mixtures and blends thereof.

5. The composition of claim 1, wherein the silicone comprises dimethicone.

6. The composition of claim 1, wherein the quaternium is a blend of behentrimonium methosulfate and cetearyl alcohol.

7. The composition of claim 1, further comprising a vegetable oil.

8. The composition of claim 7, wherein the vegetable oil comprises an avocado oil.

9. The composition of claim 1, further comprising at least one material selected from the group consisting of ascorbyl palmitate, tocopherol, aloe barbadensis, aloe vera extract, persea gratissima, avocado oil, ethylhexyl palmitate, lecithin, capric triglyceride, caprylic triglyceride, isopropylparaben, isobutylparaben, butylparaben, methylparaben, alcohol, BHT, and blends and mixtures thereof.

10. The composition of claim 1, wherein the composition comprises an emulsion.

11. A method consisting essentially of:
applying a quantity of a composition to a portion of human skin, the composition comprising a glycol, a silicone, a quaternium, and 0.2% to 1% by weight of a polymer viscosity modulator wherein the polymer viscosity modulator is a blend of polyquaternium-37 propylene glycol dicaprylate/dicaprate and PPG-1 trideceth-6, wherein the composition is free of an alpha-hydroxy acid and has a pH of less than 3.5;
rubbing the skin to distribute the composition over the skin to exfoliate and promote cell turnover of the skin without the use of alpha-hydroxy acid; and
leaving the composition on the skin.

12. A composition consisting essentially of:
a glycol;
a silicone, wherein the amount of silicone present in the composition is 4% to 30% by weight;
a quaternium;
a polymer viscosity modulator wherein the polymer viscosity modulator is a blend of polyquaternium-37, propylene glycol dicaprylate/dicaprate and PPG-1 trideceth-6;
water, wherein the amount of water present in the composition is 60% to 90% by weight; and
wherein the composition is suitable for being left on the skin and has a pH of less than 3.5.

13. The composition of claim 12 wherein the composition is in the form of an oil in water emulsion.

14. The composition of claim 11 wherein the composition is in the form of a lotion.

15. The composition of claim 11 wherein the composition is in the form of an oil in water emulsion.

* * * * *